(12) United States Patent
Raybin et al.

(10) Patent No.: US 9,895,153 B2
(45) Date of Patent: Feb. 20, 2018

(54) HEMOSTATIC CLIP WITH NEEDLE PASSER

(71) Applicant: Boston Scientific Scimed, Inc., Maple Grove, MN (US)

(72) Inventors: Samuel Raybin, Marlborough, MA (US); Paul Smith, Smithfield, RI (US); Norman C May, Northborough, MA (US); Naroun Suon, Lawrence, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 214 days.

(21) Appl. No.: 14/755,923

(22) Filed: Jun. 30, 2015

(65) Prior Publication Data

US 2016/0000433 A1 Jan. 7, 2016

Related U.S. Application Data

(60) Provisional application No. 62/019,588, filed on Jul. 1, 2014.

(51) Int. Cl.
*A61B 17/062* (2006.01)
*A61B 17/04* (2006.01)
(Continued)

(52) U.S. Cl.
CPC .... *A61B 17/1227* (2013.01); *A61B 17/00234* (2013.01); *A61B 17/0469* (2013.01);
(Continued)

(58) Field of Classification Search
CPC ............ A61B 17/0467; A61B 17/0469; A61B 17/0485; A61B 17/0487; A61B 17/062;
(Continued)

(56) References Cited

U.S. PATENT DOCUMENTS 3,958,576 A * 5/1976 Komiya ............... A61B 17/083
24/456
5,181,919 A * 1/1993 Bergman ........... A61B 17/0469
606/139
(Continued)

FOREIGN PATENT DOCUMENTS

EP 2 462 877 6/2012
JP 2009279395 12/2009

*Primary Examiner* — Ryan J Severson
(74) *Attorney, Agent, or Firm* — Fay Kaplun & Marcin, LLP (57) ABSTRACT

A device for treating a tissue opening includes a capsule extending longitudinally from a proximal end to a distal end and including a lumen extending therethrough; a pair of arms movably housed within the lumen of the capsule such that the pair of arms are movable between an open configuration and a closed configuration, the pair of arms being biased toward the open configuration such that when the pair of arms are moved distally with respect to the capsule, distal ends of the pair of arms are separated from one another to receive target tissue therebetween; a needle releasably connected to a first one of the pair of arms, the needle extending laterally inward toward a second one of the pair of arms and including a connecting structure extending along a portion thereof, the second one of the pair of arms including an opening located so that, when the pair of arms are moved to the closed configuration, the connecting structure of the needle engages the opening; and a suture extending from a portion of the needle proximally through the capsule.

16 Claims, 5 Drawing Sheets

(51) Int. Cl.
  *A61B 17/122* (2006.01)
  *A61B 17/00* (2006.01)
  *A61B 17/08* (2006.01)
  *A61B 17/10* (2006.01)
  *A61B 17/128* (2006.01)
  *A61B 17/06* (2006.01)
  *A61B 90/00* (2016.01)

(52) U.S. Cl.
  CPC ........ *A61B 17/062* (2013.01); *A61B 17/0625* (2013.01); *A61B 17/083* (2013.01); *A61B 17/10* (2013.01); *A61B 17/1285* (2013.01); *A61B 17/0467* (2013.01); *A61B 2017/00278* (2013.01); *A61B 2017/00353* (2013.01); *A61B 2017/00358* (2013.01); *A61B 2017/06047* (2013.01); *A61B 2017/086* (2013.01); *A61B 2090/037* (2016.02)

(58) Field of Classification Search
  CPC ... A61B 17/0625; A61B 17/08; A61B 17/083; A61B 17/10; A61B 17/122; A61B 17/1227; A61B 17/128; A61B 17/1285; A61B 2017/00349; A61B 2017/00353; A61B 2017/047; A61B 2017/0475; A61B 2017/0477; A61B 2017/0488; A61B 2017/0496; A61B 2017/081; A61B 2090/037
  See application file for complete search history.

(56) References Cited

U.S. PATENT DOCUMENTS

| | | | |
|---|---|---|---|
| 5,304,183 A * | 4/1994 | Gourlay | A61B 17/00234 227/901 |
| 5,454,823 A * | 10/1995 | Richardson | A61B 17/0469 606/145 |
| 5,522,820 A * | 6/1996 | Caspari | A61B 17/0625 606/139 |
| 5,690,653 A * | 11/1997 | Richardson | A61B 17/0469 606/148 |
| 5,730,747 A * | 3/1998 | Ek | A61B 17/0469 606/139 |
| 5,947,982 A * | 9/1999 | Duran | A61B 17/0625 606/139 |
| 5,980,538 A * | 11/1999 | Fuchs | A61B 17/0469 606/139 |
| 7,357,805 B2 * | 4/2008 | Masuda | A61B 17/122 606/139 |
| 7,377,926 B2 * | 5/2008 | Topper | A61B 17/0469 606/144 |
| 7,381,212 B2 * | 6/2008 | Topper | A61B 17/0469 606/223 |
| 7,494,461 B2 * | 2/2009 | Wells | A61B 17/122 600/104 |
| 7,572,265 B2 * | 8/2009 | Stone | A61B 17/0625 606/139 |
| 7,931,578 B2 * | 4/2011 | Whayne | A61B 17/0401 600/16 |
| 7,972,344 B2 * | 7/2011 | Murray | A61B 17/0469 606/144 |
| 8,057,489 B2 * | 11/2011 | Stone | A61B 17/0469 606/139 |
| 8,177,794 B2 * | 5/2012 | Cabrera | A61B 17/04 606/144 |
| 8,246,637 B2 * | 8/2012 | Viola | A61B 17/04 606/144 |
| 8,282,656 B2 * | 10/2012 | Hart | A61B 17/0469 606/139 |
| 8,292,905 B2 * | 10/2012 | Taylor | A61B 17/04 606/144 |
| 8,292,906 B2 * | 10/2012 | Taylor | A61B 17/04 606/144 |
| 8,337,515 B2 * | 12/2012 | Viola | A61B 17/04 606/144 |
| 8,372,090 B2 * | 2/2013 | Wingardner | A61B 17/04 606/139 |
| 8,460,275 B2 * | 6/2013 | Taylor | A61B 17/04 227/176.1 |
| 8,460,318 B2 * | 6/2013 | Murray | A61B 17/0469 606/144 |
| 8,496,674 B2 * | 7/2013 | Cabrera | A61B 17/04 606/144 |
| 8,506,581 B2 * | 8/2013 | Wingardner, III | A61B 17/04 606/139 |
| 8,591,526 B2 * | 11/2013 | Cronin | A61B 17/0469 606/144 |
| 8,628,545 B2 * | 1/2014 | Cabrera | A61B 17/0469 606/144 |
| 8,636,752 B2 * | 1/2014 | Cabrera | A61B 17/04 606/144 |
| 8,747,424 B2 * | 6/2014 | Taylor | A61B 17/04 606/144 |
| 8,968,339 B2 * | 3/2015 | Malkowski | A61B 17/06066 606/144 |
| 8,968,340 B2 * | 3/2015 | Chowaniec | A61B 17/0469 606/144 |
| 8,968,342 B2 * | 3/2015 | Wingardner, III | A61B 17/04 606/139 |
| 8,986,326 B2 * | 3/2015 | Satake | A61B 17/08 606/142 |
| 9,113,860 B2 * | 8/2015 | Viola | A61B 17/04 |
| 9,271,723 B2 * | 3/2016 | Taylor | A61B 17/04 |
| 9,393,010 B2 * | 7/2016 | Murray | A61B 17/0469 |
| 2003/0065337 A1 * | 4/2003 | Topper | A61B 17/0469 606/144 |
| 2004/0199184 A1 * | 10/2004 | Topper | A61B 17/0469 606/144 |
| 2005/0049618 A1 * | 3/2005 | Masuda | A61B 17/122 606/151 |
| 2005/0267529 A1 * | 12/2005 | Crockett | A61B 17/00234 606/215 |
| 2006/0004388 A1 * | 1/2006 | Whayne | A61B 17/0401 606/151 |
| 2006/0020162 A1 * | 1/2006 | Whayne | A61B 17/0401 600/37 |
| 2007/0093857 A1 * | 4/2007 | Rogers | A61B 17/0644 606/142 |
| 2007/0225735 A1 * | 9/2007 | Stone | A61B 17/0625 606/144 |
| 2008/0208221 A1 * | 8/2008 | Murray | A61B 17/0469 606/145 |
| 2008/0255427 A1 * | 10/2008 | Satake | A61B 17/08 600/204 |
| 2009/0306684 A1 * | 12/2009 | Stone | A61B 17/0469 606/145 |
| 2009/0312773 A1 * | 12/2009 | Cabrera | A61B 17/0469 606/144 |
| 2010/0010512 A1 * | 1/2010 | Taylor | A61B 17/04 606/144 |
| 2010/0030028 A1 * | 2/2010 | Cabrera | A61B 17/04 600/127 |
| 2010/0030238 A1 * | 2/2010 | Viola | A61B 17/04 606/144 |
| 2010/0049219 A1 * | 2/2010 | Cronin | A61B 17/0469 606/144 |
| 2010/0076460 A1 * | 3/2010 | Taylor | A61B 17/04 606/144 |
| 2010/0076461 A1 * | 3/2010 | Viola | A61B 17/04 606/144 |
| 2010/0094083 A1 * | 4/2010 | Taylor | A61B 17/04 600/106 |
| 2010/0121352 A1 * | 5/2010 | Murray | A61B 17/0469 606/144 |
| 2010/0137887 A1 * | 6/2010 | Crockett | A61B 17/00234 606/144 |

(56) References Cited

U.S. PATENT DOCUMENTS

| | | | |
|---|---|---|---|
| 2010/0217282 A1* | 8/2010 | Cabrera | A61B 17/04 606/144 |
| 2010/0228270 A1* | 9/2010 | Bogart | A61B 17/0469 606/144 |
| 2010/0274265 A1* | 10/2010 | Wingardner | A61B 17/04 606/144 |
| 2010/0305581 A1* | 12/2010 | Hart | A61B 17/0469 606/139 |
| 2012/0150197 A1* | 6/2012 | Malkowski | A61B 17/0625 606/144 |
| 2012/0158020 A1* | 6/2012 | Crockett | A61B 17/00234 606/139 |
| 2012/0215234 A1* | 8/2012 | Chowaniec | A61B 17/0469 606/144 |
| 2012/0277769 A1* | 11/2012 | Cabrera | A61B 17/04 606/147 |
| 2013/0035703 A1* | 2/2013 | Taylor | A61B 17/04 606/144 |
| 2013/0110136 A1* | 5/2013 | Viola | A61B 17/04 606/145 |
| 2013/0123815 A1* | 5/2013 | Wingardner, III | A61B 17/04 606/145 |
| 2013/0261644 A1* | 10/2013 | Taylor | A61B 17/04 606/144 |
| 2013/0317525 A1* | 11/2013 | Wingardner, III | A61B 17/04 606/145 |
| 2013/0345725 A1* | 12/2013 | Murray | A61B 17/0469 606/147 |
| 2016/0000433 A1* | 1/2016 | Raybin | A61B 17/0469 606/145 |
| 2016/0000445 A1* | 1/2016 | Raybin | A61B 17/0469 606/157 |
| 2016/0174967 A1* | 6/2016 | Taylor | A61B 17/04 606/144 |

* cited by examiner

HEMOSTATIC CLIP WITH NEEDLE PASSER

PRIORITY CLAIM

The present disclosure claims priority to U.S. Provisional Patent Application Ser. No. 62/019,588 filed Jul. 1, 2014; the disclosure of which is incorporated herewith by reference.

BACKGROUND

Physicians have become more willing to perform more aggressive interventional and therapeutic endoscopic procedures including, for example, removal of larger lesions (e.g., cancerous masses), tunneling under mucosal layers in the gastro-intestinal (GI) tract to treat tissues below the mucosa, full thickness removal of tissue, inserting devices through the GI tract and then penetrating the GI organ to treat tissue outside the GI tract, and endoscopic treatment/repair of post-surgical issues (e.g., post-surgical leaks, breakdown of surgical staple lines, anastomotic leaks). These procedures may increase the risk of perforating the wall of the GI tract, or may require closure of the GI tract wall as part of the procedure. Endoscopic closure reduces cost and may reduce the trauma and inconvenience associated with these procedures. However, conventional tissue closure devices may be insufficient to close certain perforations.

SUMMARY

The present disclosure is directed to a device for treating a tissue opening, comprising a capsule extending longitudinally from a proximal end to a distal end and including a lumen extending therethrough, a pair of arms movably housed within the lumen of the capsule such that the arms are movable between an open configuration and a closed configuration. The arms being biased toward the open configuration such that when the arms are moved distally with respect to the capsule, distal ends of the arms are separated from one another to receive target tissue therebetween. The device furthermore comprises needle releasably connected to a first one of the arms, the needle extending laterally inward toward a second one of the arms and including a connecting structure extending along a portion thereof. The second one of the arms including an opening located so that, when the arms are moved to the closed configuration, the connecting structure of the needle engages the opening, and a suture extending from a portion of the needle proximally through the capsule.

In an embodiment, wherein the needle may be connected to the first one of the arms via a frangible link designed to break when the connecting structure of the needle engages the opening and the needle disengages from the first arm when the arms are moved to the open configuration.

In an embodiment, the connecting feature may include barbs.

In an embodiment, the opening of the second one of the arms may include a barb feature and the connecting feature is a groove extending around a portion of the needle for receiving the barb feature.

In an embodiment, the device may further comprise a control member connected to the arms for moving the arms between the open and the closed configuration.

In an embodiment, the device may further comprise a handle assembly connected to the capsule via a flexible member which is releasably coupled to the capsule, the control member extending through the flexible member to the handle assembly.

In an embodiment, the device may further comprise a locking mechanism for locking the arms in the capsule in the closed configuration.

In an embodiment, when the arms are locked within the capsule, the suture may become wedged so that it is restrained from distal translation.

In an embodiment, the device may further comprise a cutting feature cutting a portion of the suture extending proximally of a wedged portion of the suture.

The present disclosure is also directed to a device for closing a tissue opening, comprising a clip including a pair of arms movable between an open configuration in which distal ends of the arms are separated from one another to receive target tissue therebetween and a closed configuration in which the arms drawn toward one another to grip the target tissue therebetween and a needle releasably connected to a first one of the arms, the needle extending laterally inward toward a second one of the arms and including a connecting structure extending along a portion thereof, the second one of the arms including an opening extending laterally therethrough located so that, when the arms are moved to the closed configuration, the connecting structure of the needle engages the opening, the being frangible link designed to disengage when the arms are moved to the open configuration after the connecting structure of the needle has engaged the opening along with a suture extending from a portion of the needle proximally through a portion of the device.

In an embodiment, the device may further comprise a capsule extending longitudinally from a proximal end to a distal end and including a lumen extending therethrough, the lumen slidably receiving proximal ends of the arms, the arms being biased toward the open configuration such that moving the arms distally with respect to the capsule permits distal ends of the arms to separate from one another, in the closed configuration, the arms being drawn proximally into the capsule so that contact with the capsule draws the arms into the closed configuration.

In an embodiment, the device may further comprise a control member connected to the arms for moving the arms between the open and the closed configurations and a handle assembly connected to the capsule via a flexible member which is releasably coupled to the capsule, the control member extending through the flexible member to the handle assembly.

In an embodiment, the device may further comprise a locking mechanism for locking the arms in the closed configuration.

In an embodiment, when the arms are locked within the capsule, the suture may become wedged so that it is restrained from distal translation In an embodiment, the device may further comprise a cutting feature cutting a portion of the suture extending proximally of a wedged portion of the suture.

The present disclosure is also directed to a method for treating a tissue opening, comprising inserting a clip to a target area within a patient body, the clip including a pair of arms movable between an open configuration in which distal ends of the arms are separated from one another and a closed configuration in which distal ends of the arms are drawn toward one another to grip tissue received therebetween, and a needle releasably connected to a first one of the arms, the needle extending toward a second one of the arms, positioning the arms over a first portion of tissue along a tissue opening with the clip in the open configuration such that the first portion of tissue is received between the distal ends of the arms, moving the arms to the closed configuration such that the needle pierces the first portion of tissue and engages an opening extending laterally through a second one of the arms, and moving the arms to the open configuration such that the frangible link breaks, the needle remains engaged to the opening of the second one of the arms and a suture extending proximally from a portion of the needle is threaded through the first portion of tissue.

BRIEF DESCRIPTION

DETAILED DESCRIPTION

The present disclosure may be further understood with reference to the following description and the appended drawings, wherein like elements are referred to with the same reference numerals. The present disclosure relates to devices for tissue closure and, in particular, to an endoscopic tissue closure device. Exemplary embodiments of the present disclosure describe an endoscopic tissue closure device comprising a clip and a needle such that a suture may be passed through a first portion of tissue along a tissue opening and the clip may be applied over a second portion of tissue along the tissue opening substantially opposing the first portion so that the first portion of tissue may be drawn toward the second portion by drawing the suture proximally relative to the clip. It should be noted that the terms "proximal" and "distal" as used herein, are intended to refer to a direction toward (proximal) and away from (distal) a user of the device.

As shown in FIGS. 1-10, a device 100 according to an exemplary embodiment of the present disclosure comprises a clip 102 including first and second arms 104, 106 movable between an open configuration and a closed configuration and a needle 108 extending laterally inward from the first arm 104 toward the second arm 106 to pass a suture 112 coupled to the needle 108 through a first portion of tissue 12 along a tissue opening 10. The device is inserted to a target spot within the body via, for example, a body lumen accessed via a naturally occurring bodily orifice. The device 100, however, may be inserted into the patient body in any of a number of different ways such as, for example, via a flexible endoscope, or through a rigid tube, etc. The clip 102 is movable between a closed configuration in which the first and second arms 104, 106, respectively, are drawn together in contact with one another and an open configuration in which distal ends 114, 115 of the first and second arms 104, 106, respectively, are separated from one another to permit a portion of tissue to be received therebetween. In the closed configuration, the distal ends 114, 115 of the arms 104, 106 are drawn toward one another to grip tissue received therebetween. The second arm 106 includes an opening 110 such as a slot or hole extending laterally therethrough. The opening 110 is sized and shaped to receive a portion of the needle 108 therein. The needle 108 is attached to the first arm 104 via a frangible link 116 such that when the arms 104, 106 are moved toward the closed configuration over the first portion of tissue 12, the needle 108 is passed through the first portion of tissue 12 into the opening 110 and locked therein so that when the clip 102 is moved once again to the open configuration, the frangible link 116 is broken leaving the needle 108 lodged in the second arm 110. As the clip 102 moves to the open configuration, the suture 112 is drawn through the first portion of tissue 12. The clip 102 is then opened and repositioned over a second portion of tissue 14 (e.g., a second portion of tissue on the periphery of the tissue opening 10 substantially opposite the first portion 12). Once the clip 102 has been repositioned as desired, the clip 102 is moved to the closed configuration to grip the second portion of tissue 14. The loop of suture 112 is then tightened to draw the first portion of tissue 12, through which the suture 112 is passed, toward the clip 102 until the first portion 12 is drawn against the second portion 14 closing the tissue opening 10.

The clip 102 may further include a capsule 118 in which the first and second arms 104, 106 are movably housed. The capsule 118 extends longitudinally from a proximal end 124 to a distal end 126 and includes a lumen 128 extending therethrough. Proximal ends of the first and second arms 104, 106 are slidably received within the lumen 128 so that the clip 102 may be moved between the open and the closed configurations. The first and second arms 104, 106 may be biased toward the open configuration such that when the first and second arms 104, 106 are moved distally out of the capsule 118, distal ends 114, 115 of the arms 104, 106 extend away from one another to the open configuration. When the first and second arms 104, 106 are drawn proximally into the capsule 118, however, the first and second arms 104, 106 are constrained via an interior surface 132 of the capsule 118 so that distal ends 114, 115 of the arms 104, 106 are drawn toward one another into the closed configuration. Distal ends 114, 115 may include gripping features such as, for example, teeth or tines extending laterally inward for gripping the tissue received therebetween. The clip 102 may be coupled to a proximal portion of the device 100 (not shown) via a control member or other device which permits a user to move the clip 102 proximally and distally relative to the capsule 118 so that the clip 102 moves between the open and closed configurations.

In one embodiment, the capsule 118 may be coupled to a handle assembly (not shown), which remains outside of a patient body, via a flexible member to facilitate insertion of the clip 102 to a target area within the patient body through even tortuous paths of the body. The arms 104, 106 are moved with respect to the capsule 118 via the control member coupled to a proximal end of the arms 104, 106 and extending proximally through the flexible member to the handle assembly. The arms 104, 106 may be moved distally and proximally with respect to the capsule 118 between the open and closed configurations by moving the control member distally and proximally, respectively, via an actuator of the handle assembly. Once in the closed configuration, the control member may be drawn further proximally to lock the clip 102 in the closed configuration and disengage the clip 102 from the proximal portion of the device 100. For example, the clip 102 may be locked in the closed configuration by engagement between a portion of the clip 102 and a locking feature of the capsule 118 and disengaged from the proximal portion of the device by the separation of a frangible link substantially as described in U.S. Pat. No. 7,494,461 issued on Feb. 24, 2009 to Wells et al. In particular, when the control member of this embodiment is drawn proximally after a point of maximum proximal withdrawal of the clip 102 into the capsule 118, increased tension on the control member causes disengagement of the control member from the arms 104, 106, causing a bushing which connects the capsule 118 to the flexible member to become disengaged therefrom. The structural features of the clip 102, however, are not limited to those described in U.S. Pat. No. 7,494,461 and that the clip 102 may be deployed in the body in any of a number of ways via the further proximal motion of the control member with respect to the clip 102.

Figure 7:
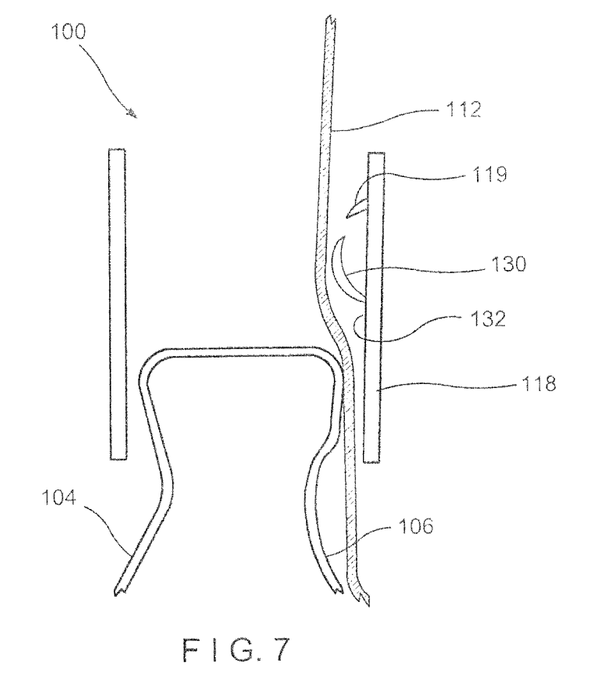
FIG. 7 shows a longitudinal cross-sectional view of a distal portion of the device of FIG. 1, in an unlocked configuration.
Figure 8:
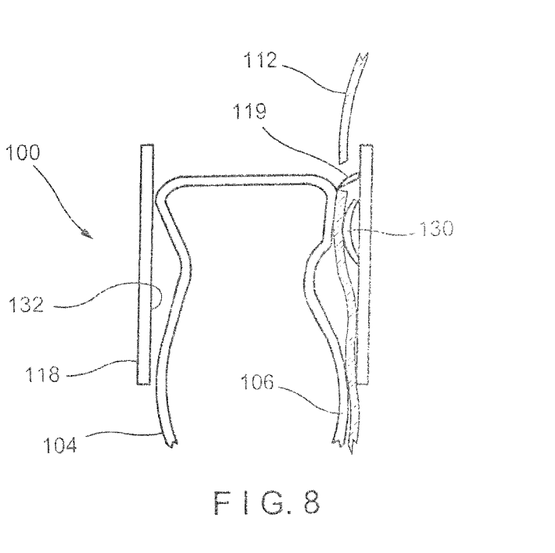
FIG. 8 shows a longitudinal cross-sectional view of the distal portion of the device of FIG. 1, in a locked configuration.

As shown in FIGS. 7-8, the clip 102 further includes a wedge feature 130 which wedges a portion of the suture 112 within the capsule 118. For example, the suture 112 may be wedged between one of the arms 104, 106 and the interior surface 132 of the capsule 118, when the clip 102 is in the locked configuration. A distal portion of the capsule 118 may be sized and shaped such that when the arms 104, 106 are drawn into the locked configuration, the arms 104, 106 and the capsule 118 form a friction fit with the portion of the suture 112 received therebetween locked therein. The capsule 118 may further include a cutting feature 119 along the interior surface 132 thereof for cutting a portion of the suture 112 extending proximally from the wedge. The cutting feature 119 of this embodiment is positioned on a portion of the capsule 118 proximal of the wedge feature. The cutting feature 119 may include, for example, a sharpened protrusion extending laterally inward and distally from the interior surface 132 of the capsule 118.

The needle 108 extends from a first end 120 attached to the first arm 104 via the frangible link 116 to a second end 122 extending laterally from the first arm 104 toward the second arm 106. The frangible link 116 may include, for example, a tight friction fit between the needle 108 and an opening in the first arm 104, an adhesive, weld, or solder joint designed to fail when subject to a force exceeding a predetermined threshold level. The frangible link 116 may include any of a variety of coupling mechanisms so long as the frangible link 116 fails when subject to a force exceeding the predetermined threshold level. Although this exemplary aspect is described and shown as including a frangible link 116 connecting the needle 108 to the first arm 104, the needle 108 may alternatively be connected to the first arm 104 via a releasable coupling. For example, the needle 108 may releasably engage a needle engaging feature in the first arm 104. The needle 108 may be released from this needle engaging feature via a force applied to the needle 108. The force may be, for example, a torsional force applied to the needle 108 by the second arm 106, which causes the needle 108 to rotate out of engagement with the needle engaging feature. Alternatively, the needle 108 may be actively released from the first arm 104, for example, by the user by means of a trigger mechanism of the like.

Figure 9:
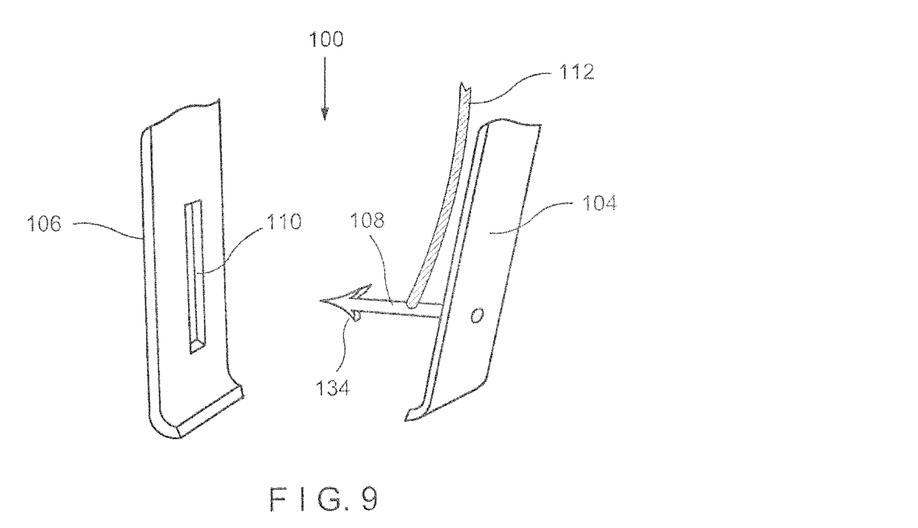
FIG. 9 shows a perspective view of arms of the clip of the device of FIG. 1, including a needle.
Figure 10:
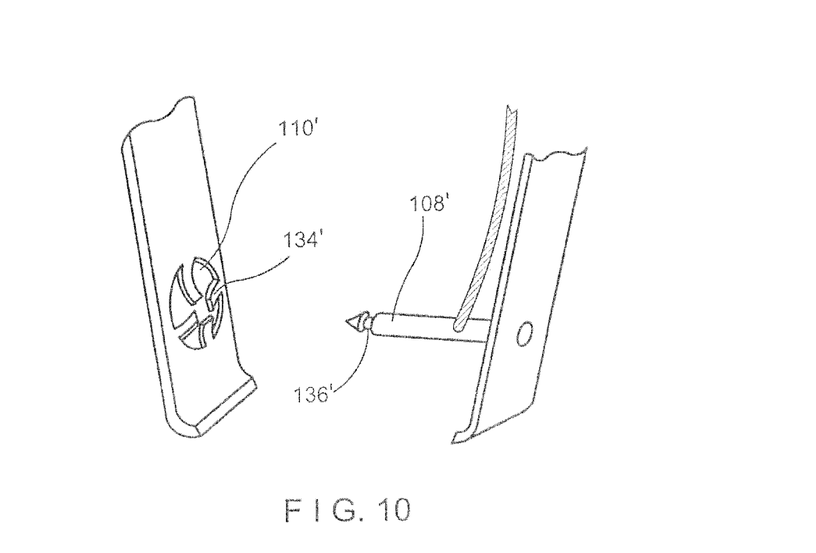
FIG. 10 shows a perspective view of arms of a clip according to an alternate embodiment of the device of FIG. 1.

As shown in FIG. 9, a portion of the needle 108 includes barbs 134 therealong so that when the needle 108 is received within the opening 110 extending laterally through the second arm 106, the needle 108 engages the opening 110 so that the needle 108 is locked therewithin. In another embodiment, as shown in FIG. 10, the barb features 134' may be included in the opening 110' so that when the needle 108' is received therewithin, the opening 110' engages a groove 136' or other corresponding feature of the needle 108'. Although the exemplary embodiments describe barbs, the needle 108 and the opening 110 of the second arm 106 may include any of a variety of corresponding locking features so long as the needle 108 is locked within the opening 110 when received therein.

The suture 112 extends from a distal end 120 connected to the needle 108 to a proximal end (not shown) extending proximally through the capsule 118 and the proximal portion of the device 100 to the handle assembly. The suture 112 is slidably received within the capsule 118 so that the suture 112 may be slackened and tightened, as desired. The proximal end of the suture 112 may be coupled to an actuating feature of the handle assembly so that the suture 112 may be tightened via the actuating feature on the handle assembly. Alternatively, the proximal end of the suture 112 may extend from the handle assembly so that the user may draw the proximal end proximally with respect to the device 100 to tighten the suture 112. The distal end 120 of the suture 112 should be connected to a portion of the needle 108 between the locking feature (e.g., barbs) of the needle 108 and the first end 120 so that locking the needle 108 within the opening 110 does not interfere with the slackening and tightening of the suture 112.

Figure 1:
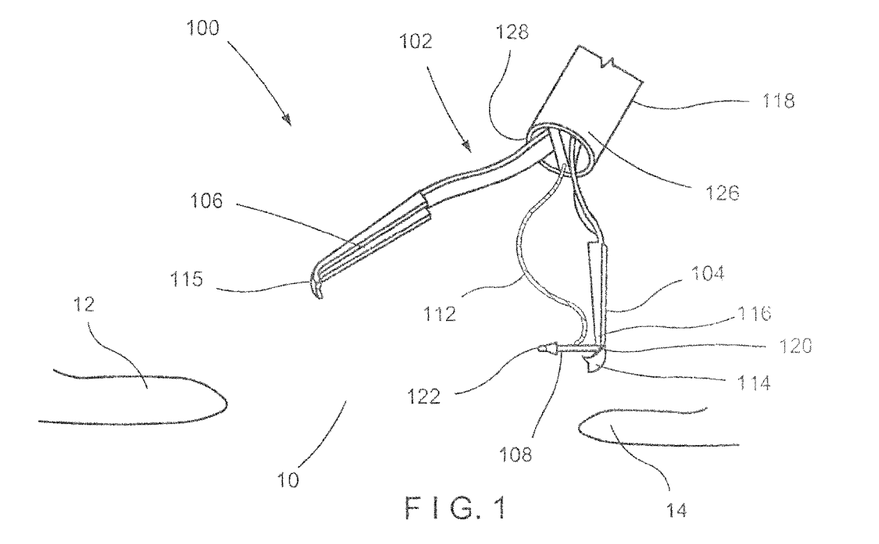
FIG. 1 shows a perspective view of a device according to an exemplary embodiment of the present disclosure, in a first configuration.

According to a method using the device 100, the clip 102, with the needle 108 connected to the first arm 104, is inserted to a target area in the patient body through, for example, a working channel of an endoscope. The clip 102 may be inserted through the working channel in an insertion configuration with the handle assembly remaining outside the patient's body. In this insertion configuration, the first and second arms 104, 106 are drawn toward one another with the needle 108 connected to the first arm 104. The needle 108, however, is prevented from engaging the second arm 106. Once the clip 102 has reached the tissue opening 10 to be closed, the clip 102 is moved to the open configuration by moving the clip arms 104, 106 distally with respect to the capsule 118 so that the arms 104, 106 are permitted to revert to their biased open position, as shown in FIG. 1. In the open configuration, the arms 104, 106 are positioned so that the first portion of tissue 12 may be received therebetween.

Figure 2:
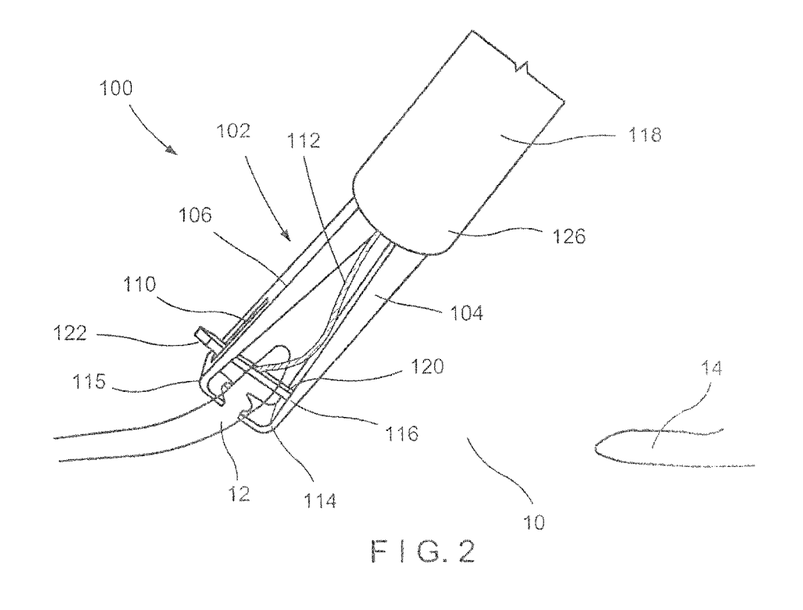
FIG. 2 shows another perspective view of the device of FIG. 1, a clip of the device gripping a first portion of tissue of a tissue opening.
Figure 3:
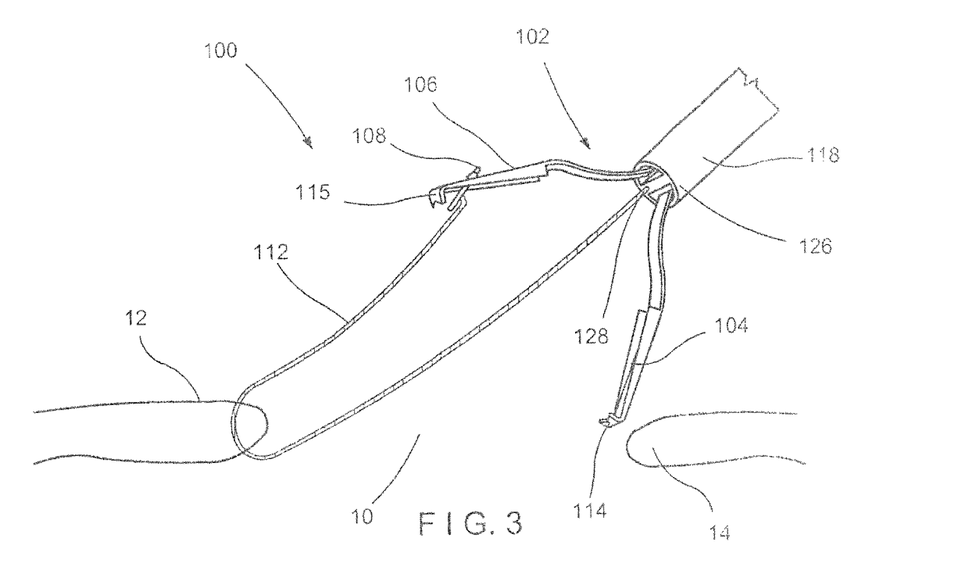
FIG. 3 shows another perspective view of the device of FIG. 1, in a second configuration.

Once positioned, as desired, the clip 102 is moved to the closed configuration to grip the first portion of tissue 12 between arms 104, 106 by drawing the clip arms 104, 106 into the capsule 118 so that the arms 104, 106 are constrained thereby. As the clip 102 is moved to the closed configuration, as shown in FIG. 2, the needle 108 extending laterally from the first arm 104 passes through the first portion of tissue 12 and engages the opening 110 of the second arm 106. Prior to the needle 108 engaging the opening 110 of the second arm 106, however, the arms 104, 106 may be moved between the open and closed positions to adjust the placement of the arms 104, 106 over tissue, as desired. This movement may be controlled by a user interface having incremental closing positions controlled to prevent premature engagement of the needle 108 or via tactile features that have threshold forces to actuate between states. Once the needle 108 has engaged the opening 110 of the second arm 106, however, the clip 102 is moved to the open configuration so that distal ends 114, 115 of the arms 104, 106 are once again separated from one another. Since the needle 108 is locked within the opening 110 of the second arm 106, the separation of the distal ends 114, 115 causes the frangible link 116 connecting the first end 120 of the needle 108 to the first arm 104 to break. The needle 108, however, remains locked in the opening 110 so that the suture 112 is passed through the first portion of tissue 12. As the clip 102 is moved to the open configuration, the clip 102 is also moved proximally relative to the first portion of the tissue 12, causing the clip 102 to be moved proximally with respect to the suture 112, such that a slack in the suture 112 is formed, as shown in FIG. 3.

Figure 4:
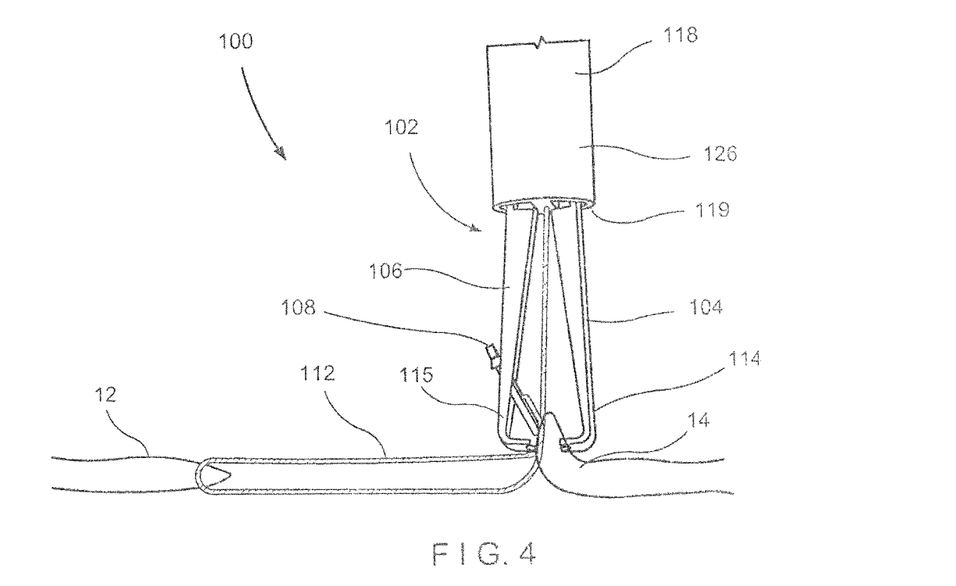
FIG. 4 shows a side view of the device of FIG. 1, the clip gripping a second portion of tissue of the tissue opening.
Figure 5:
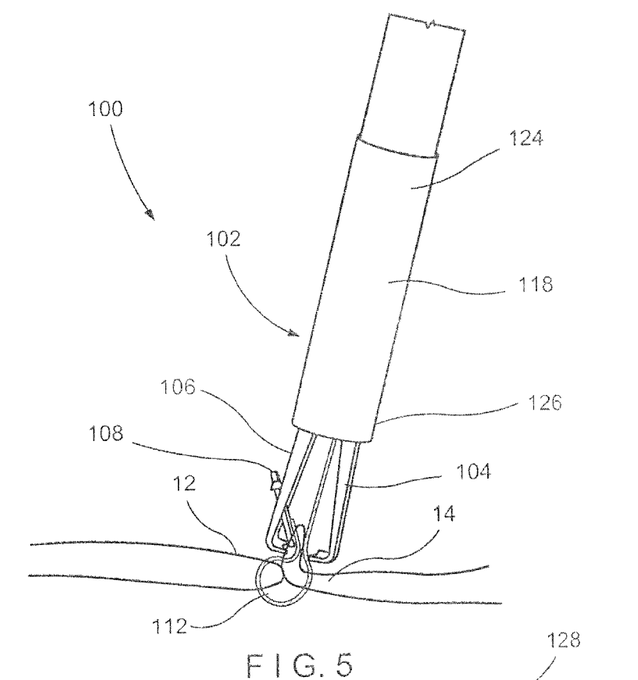
FIG. 5 shows a perspective view of the device of FIG. 1, with the first and second tissue portions drawn toward one another.

The clip 102 is then moved to the second portion of tissue 14 substantially opposing the first portion 12 and positioned thereover such that the second portion 14 is received between the arms 104, 106. As shown in FIG. 4, once the clip 102 has been positioned over the second portion, as desired, the clip 102 is moved to the closed configuration to grip the second portion of tissue 14 between the arms 104, 106. The suture 112 is then drawn proximally with respect to the clip 102, drawing the first portion of tissue 12 toward the second portion of tissue 14 to close the tissue opening 10, as shown in FIG. 5. Although the exemplary embodiments show and describe the clip 102 as being moved to the locked configuration once the clip 102 has been clipped over the second portion of tissue 14 and the first portion of the tissue 12 has been drawn theretoward via the suture 112, the clip 102 may be repositioned prior to locking, if so desired. For example, clip arms 104, 106 may be repositioned to get a better grasp of the second portion of tissue 14.

Figure 6:
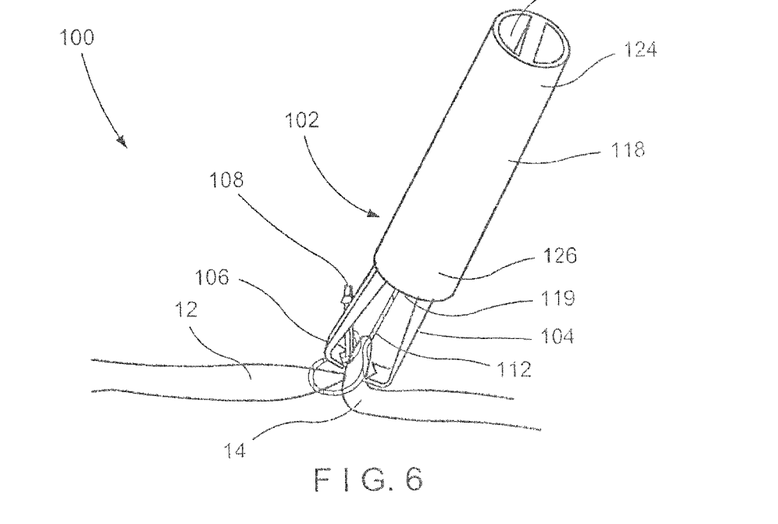
FIG. 6 shows another perspective view of the device of FIG. 1, in a locked configuration.

In another example, the clip 102 may be repositioned to extend over both the first and second portions of tissue 12, 14, once the first and second portions of tissue 12, 14 have been drawn toward one another, so that the clip 102 grips both portions of tissue 12, 14. Once the tissue opening 10 is closed, as desired, the clip 102 may be locked, as shown in FIG. 6, by drawing the control member further proximally with respect to the clip 102. As described above, moving the clip 102 to the locked configuration will also cause a portion of the suture 112 to become wedged between one of the clip arms 104, 106 and the interior of the capsule 118. Upon wedging of the suture 112 between the clip arms 104, 106, a portion of the suture extending proximally of the wedge is cut therefrom via the cutting feature along the interior of the capsule 118. The proximal portion of the device 100 is then removed from the body such that only the clip 102, the needle 108, and a distal portion of the suture 112 remain within the body to hold the tissue opening 10 in the closed position.

While embodiments have been described above, a number of modifications and changes may be made without departing from the scope of the disclosure. Thus, it is intended that the present disclosure cover modifications and variations provided that they come within the scope of the appended claims and their equivalents.

What is claimed is:

1. A device for treating a tissue opening, comprising:
   a capsule extending longitudinally from a proximal end to a distal end and including a lumen extending therethrough;
   a pair of arms movably housed within the lumen of the capsule such that the pair of arms are movable between an open configuration and a closed configuration, the pair of arms being biased toward the open configuration such that when the pair of arms are moved distally with respect to the capsule, distal ends of the pair of arms are separated from one another to receive target tissue therebetween, the pair of arms configured to be locked relative to the capsule in the closed configuration;
   a needle releasably connected to a first one of the pair of arms, the needle extending laterally inward toward a second one of the pair of arms and including a connecting structure extending along a portion thereof, the second one of the pair of arms including an opening located so that, when the pair of arms are moved to the closed configuration, the connecting structure of the needle engages the opening; and
   a suture extending from a portion of the needle proximally through the capsule.

2. The device of claim 1, wherein the needle is connected to the first one of the pair of arms via a frangible link designed to break when the connecting structure of the needle engages the opening and the needle disengages from the first arm when the pair of arms are moved to the open configuration.

3. The device of claim 1, wherein the connecting structure includes barbs.

4. The device of claim 1, wherein the opening of the second one of the pair of arms includes a barb feature and the connecting structure is a groove extending around a portion of the needle for receiving the barb feature.

5. The device of claim 1, wherein, when the pair of arms are locked within the capsule, the suture becomes wedged so that it is restrained from distal translation.

6. The device of claim 5, further comprising:
   a cutting feature cutting a portion of the suture extending proximally of a wedged portion of the suture.

7. A device for closing a tissue opening, comprising:
   a clip including a pair of arms movable between an open configuration in which distal ends of the pair of arms are separated from one another to receive target tissue therebetween and a closed configuration in which the pair of arms drawn toward one another to grip the target tissue therebetween;
   a needle releasably connected to a first one of the pair of arms, the needle extending laterally inward toward a second one of the pair of arms and including a connecting structure extending along a portion thereof, the second one of the pair of arms including an opening extending laterally therethrough located so that, when the pair of arms are moved to the closed configuration, the connecting structure of the needle engages the opening, the needle being connected to the first one of the pair of arms via a frangible link designed to disengage when subject to a force exceeding a predetermined threshold level by movement of the pair of arms toward the open configuration after the connecting structure of the needle has engaged the opening; and
   a suture extending from a portion of the needle proximally through a portion of the device.

8. The device of claim 7, further comprising:
   a capsule extending longitudinally from a proximal end to a distal end and including a lumen extending therethrough, the lumen slidably receiving proximal ends of the pair of arms, the pair of arms being biased toward the open configuration such that moving the pair of arms distally with respect to the capsule permits distal ends of the pair of arms to separate from one another, in the closed configuration, the pair of arms being drawn proximally into the capsule so that contact with the capsule draws the pair of arms into the closed configuration.

9. The device of claim 8, wherein the pair of arms are configured to be locked relative to the capsule in the closed configuration.

10. The device of claim 9, wherein, when the pair of arms are locked within the capsule, the suture becomes wedged so that it is restrained from distal translation.

11. The device of claim 10, further comprising:
a cutting feature cutting a portion of the suture extending proximally of a wedged portion of the suture.

12. A method for treating a tissue opening, comprising:
inserting a clip to a target area within a patient body, the clip including a pair of arms movable between an open configuration in which distal ends of the pair of arms are separated from one another and a closed configuration in which distal ends of the pair of arms are drawn toward one another to grip tissue received therebetween, and a needle releasably connected to a first one of the pair of arms, the needle extending toward a second one of the pair of arms;
positioning the pair of arms over a first portion of tissue along a tissue opening with the clip in the open configuration such that the first portion of tissue is received between the distal ends of the pair of arms;
moving the pair of arms to the closed configuration such that the needle pierces the first portion of tissue and engages an opening extending laterally through a second one of the pair of arms; and
moving the pair of arms to the open configuration, breaking a frangible link connecting the needle to the first one of the pair of arms so that the needle remains engaged to the opening of the second one of the pair of arms and a suture extending proximally from a portion of the needle is threaded through the first portion of tissue.

13. The method of claim 12, further comprising:
after moving the pair of arms to the open configuration with the suture passed through the first portion of tissue, positioning the pair of arms over a second portion of tissue along the tissue opening substantially opposing the first portion with the clip in the open configuration with the second portion of tissue is received between the distal ends of the pair of arms;
moving the pair of arms to the closed configuration such that the pair of arms grip the second portion of tissue between distal ends of thereof.

14. The method of claim 13, further comprising:
pulling the suture proximally relative to the clip to draw the first portion of tissue toward the second portion of tissue.

15. The method of claim 14, further comprising:
locking the clip in the closed configuration.

16. The method of claim 15, wherein locking the clip includes locking the suture relative to the clip and cutting a portion of the suture extending proximally from the clip.

* * * * *